(12) United States Patent
Ho et al.

(10) Patent No.: US 10,898,164 B2
(45) Date of Patent: Jan. 26, 2021

(54) SYSTEM FOR SHAPING AND POSITIONING A TISSUE BODY

(71) Applicant: Delphinus Medical Technologies, Inc., Novi, MI (US)

(72) Inventors: Ron Ho, Mountain View, CA (US); Peter Littrup, Bloomfield Hills, MI (US); Nebojsa Duric, Bloomfield Hills, MI (US)

(73) Assignee: Delphinus Medical Technologies, Inc., Novi, MI (US)

( * ) Notice: Subject to any disclaimer, the term of this patent is extended or adjusted under 35 U.S.C. 154(b) by 490 days.

(21) Appl. No.: 15/427,857

(22) Filed: Feb. 8, 2017

(65) Prior Publication Data

US 2017/0224305 A1 Aug. 10, 2017

Related U.S. Application Data

(60) Provisional application No. 62/293,071, filed on Feb. 9, 2016.

(51) Int. Cl.
*A61B 8/08* (2006.01)
*A61B 8/00* (2006.01)
*A61B 8/15* (2006.01)

(52) U.S. Cl.
CPC ............ *A61B 8/406* (2013.01); *A61B 8/0825* (2013.01); *A61B 8/15* (2013.01); *A61B 8/4281* (2013.01); *A61B 8/4483* (2013.01)

(58) Field of Classification Search
CPC ......... A61B 8/406; A61B 8/15; A61B 8/0825; A61B 8/4483; A61B 8/4281
See application file for complete search history.

(56) References Cited

U.S. PATENT DOCUMENTS 3,608,540 A * 9/1971 Sartorius ............ A61B 10/0041
600/563
4,206,763 A 6/1980 Pedersen
6,102,857 A 8/2000 Kruger
(Continued)

FOREIGN PATENT DOCUMENTS

WO WO-2005072616 A2 8/2005
WO WO-2007147060 A2 12/2007
(Continued)

OTHER PUBLICATIONS

International Search Report and Written Opinion dated May 5, 2017 for International Application No. PCT/US2017/17035.
(Continued)

*Primary Examiner* — Luther Behringer
(74) *Attorney, Agent, or Firm* — Wilson Sonsini Goodrich & Rosati

(57) ABSTRACT

A tissue positioning system for contouring a patient tissue volume includes an axially displaceable interface having a surface configured to engage a breast or other tissue volume. A low pressure source applies a partial low pressure to the surface of the displaceable interface to secure the tissue volume to the surface, and the axially displaceable interface is biased to pull and contour the tissue volume when the tissue volume is secured to the surface. The axially displaceable interface is typically mounted on a telescoping support and the biasing is provided by the same low pressure used to secure the tissue volume.

24 Claims, 16 Drawing Sheets

(56) References Cited

U.S. PATENT DOCUMENTS

| | | | |
|---|---|---|---|
| 6,298,114 B1* | 10/2001 | Yoda | A61B 6/0414 |
| | | | 378/37 |
| 7,494,466 B2 | 2/2009 | Chauhan et al. | |
| 7,699,783 B2 | 4/2010 | Hanover et al. | |
| 7,771,360 B2 | 8/2010 | Johnson et al. | |
| 9,113,835 B2 | 8/2015 | Li | |
| 9,763,641 B2 | 9/2017 | West et al. | |
| 10,251,622 B2 | 4/2019 | Tesic et al. | |
| 2004/0064046 A1 | 4/2004 | Shehada et al. | |
| 2005/0148822 A1* | 7/2005 | Willis | A61B 17/30 |
| | | | 600/201 |
| 2006/0009693 A1 | 1/2006 | Hanover et al. | |
| 2011/0105900 A1 | 5/2011 | Entrekin | |
| 2013/0023821 A1 | 1/2013 | Khalil et al. | |
| 2013/0204136 A1* | 8/2013 | Duric | A61B 8/4494 |
| | | | 600/448 |
| 2013/0303895 A1 | 11/2013 | Littrup et al. | |
| 2014/0066772 A1 | 3/2014 | West et al. | |
| 2014/0235962 A1 | 8/2014 | Yu et al. | |
| 2014/0276068 A1* | 9/2014 | Szpak | A61B 8/406 |
| | | | 600/447 |
| 2015/0313577 A1 | 11/2015 | Duric et al. | |
| 2016/0022245 A1 | 1/2016 | Tesic et al. | |
| 2016/0030000 A1 | 2/2016 | Sandhu et al. | |
| 2016/0038123 A1 | 2/2016 | Duric et al. | |
| 2019/0083060 A1 | 3/2019 | Ho et al. | |

FOREIGN PATENT DOCUMENTS

| | | |
|---|---|---|
| WO | WO-2010092565 A1 | 8/2010 |
| WO | WO-2017040866 A1 | 3/2017 |
| WO | WO-2017139389 A1 | 8/2017 |

OTHER PUBLICATIONS

"IPRP for PCTUS201717035 dated Aug. 14, 2018".
Co-pending U.S. Appl. No. 16/285,778, filed Feb. 26, 2019.
EP17750704.3 Search Report dated Sep. 20, 2019.
U.S. Appl. No. 14/811,316 Notice of Allowance dated May 16, 2018.
U.S. Appl. No. 16/113,863 Notice of Allowance dated Nov. 30, 2018.
U.S. Appl. No. 16/123,881 Office Action dated Oct. 14, 2020.

* cited by examiner

Reflection Image comparison – left with suction device, right no suction device used – clear benefits with suction device; gel pad doesn't further distort IQ; gel pad not visible in image under regular WW/WL settings.

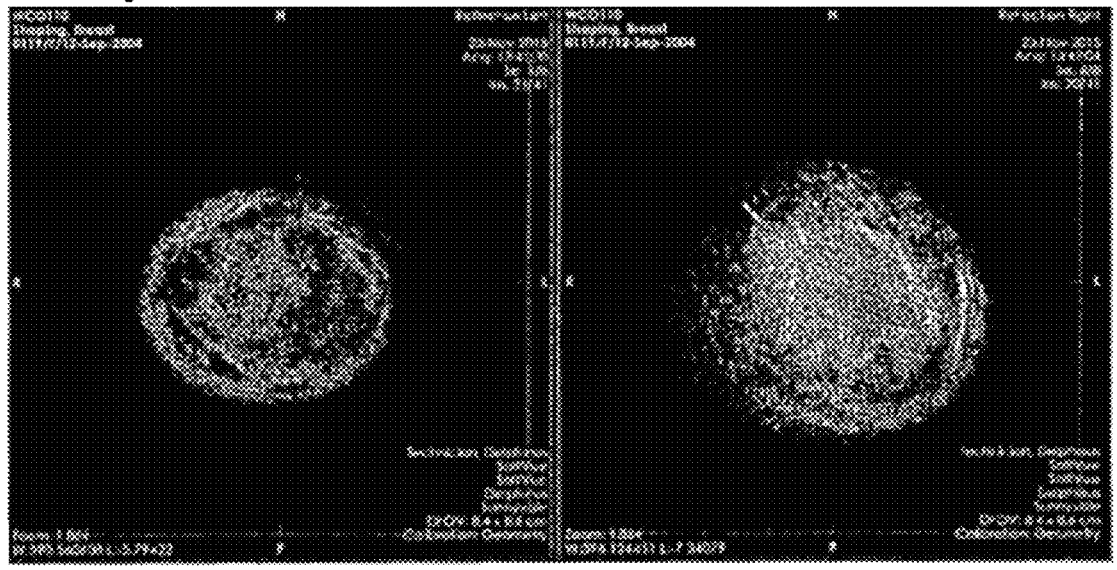

FIG. 8A

Attenuation Image comparison – left with suction device, right no suction device used – clear benefits with suction device; gel pad doesn't further distort IQ; gel pad visible in image under regular WW/WL settings but we can teach to it.

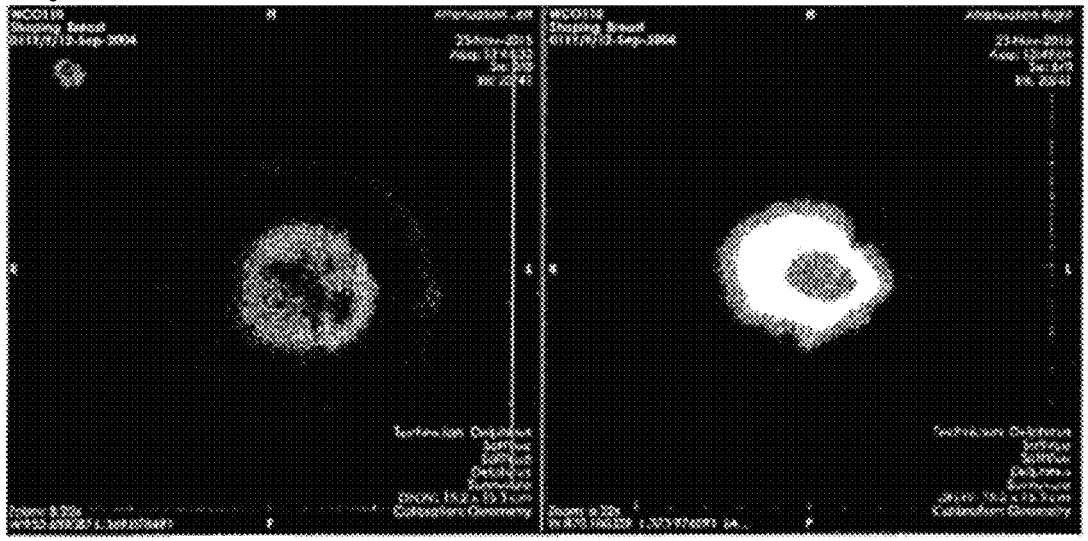

FIG. 8B

Behind the nipple reflection slice from other iterations of the gel pad idea (iteration #2, #3 on Nov 25th).

Image comparison – top row after suction device, bottom row no suction device used. With suction device, skin thickness more uniform with depth, better centration; with no suction device, skin thickness increases with depth.

SYSTEM FOR SHAPING AND POSITIONING A TISSUE BODY

CROSS-REFERENCE TO RELATED APPLICATIONS

This application claims the benefit of U.S. Provisional Application No. 62/293,071, filed Feb. 9, 2016, the full disclosure of which is incorporated herein by reference.

BACKGROUND OF THE INVENTION

1. Field of the Invention

This invention relates generally to the medical technology field, and more specifically to a new and useful system for positioning and contouring a tissue body in an imaging field.

Early detection of breast cancer and other types of cancer typically result in a higher survival rate. Despite a widely accepted standard of mammography screenings for breast cancer detection, there are many reasons that cancer is often not detected early. In particular, drawbacks of mammography include: limited performance among women with dense breast tissue, a high rate of "false alarms" that lead to unnecessary biopsies that are collectively expensive and result in emotional duress in patients, and low participation in breast screening, as a result of factors such as fear of radiation and discomfort. In particular, the mammography procedure involves compression of the breast tissue between parallel plates to increase the X-ray image quality by providing a more uniform tissue thickness and stabilizing the tissue. However, this compression is typically uncomfortable, or even painful.

A relatively new ultrasound imaging technique, referred to as ultrasound tomography, promises to be a practical alternative to mammography without tissue compression and many other drawbacks. With ultrasound tomography, the patient lies on a support surface in a prone position with a breast depending through an opening in the surface into a water bath. A ring or other ultrasonic transducer assembly is then scanned vertically to acquire the image data to be analyzed. Some of the proposed ultrasound tomography systems employ a magnetic or other device to capture the nipple region of the breast to extend and stabilize the breast during imaging. While at least partially effective, such prior breast extending apparatus can be uncomfortable, can deform the breast into a conical shape which is not optimum for imaging, do not provide repeatable shaping of the breast, and cannot accommodate breast of differing sizes.

For these reasons, it would be desirable to provide systems and methods for performing breast and other ultrasound tomography which provide improved positioning of the breast or other tissue body, improved patient comfort, and which accommodate size variations of the breasts and other tissue bodies among different patients and which allow scans to be performed in a repeatable manner in order to monitor changes in a tissue over time in an individual patient. At least some of these objectives will be met by the inventions described and claimed herein.

2. Description of the Background Art

Commonly owned US2014/0276068 and US 2013/0204136 describe an interface system for supporting a patient and exposing a depending breast in an ultrasonic tomography system. U.S. Pat. Nos. 7,771,360 and 7,699,783 describe other breast scanning systems having a magnetic capture device for a nipple region of the breast.

SUMMARY OF THE INVENTION

In a first aspect of the present invention, a tissue positioning system for contouring a patient tissue volume, such as a human breast, comprises an axially displaceable interface having a surface configured to engage and attach the tissue volume or a portion thereof. Typically, a low pressure source or appliance is configured to apply low pressure to or over the surface of the displaceable interface. The low pressure secures a target region of tissue volume, such as a nipple region of a breast, to the surface, and the axially displaceable interface is biased to pull, elongate, and/or contour the tissue volume when the tissue volume is secured to the surface. For example, elongating a breast can cause the breast to assume a generally cylindrical shape to enhance subsequent imaging, treatment, interventions, or the like.

The axially displaceable interface surface is typically formed from a gel, preferably a gel that is engineered to be acoustically/ultrasonically invisible, e.g. by formulating the gel to have a speed of sound equivalent to water at body temperature and to be disposable (single use) both for hygienic reasons. Preferred gels are cross-linking polysaccharide, such as carrageenan (seaweed derived). The gel pads may be fabricated using conventional techniques, such as mixing an aqueous solution, heating the solution, and pouring into a net-shape mold, cooling).

In a particular embodiment, the tissue positioning system may further comprise a telescoping, accordion or other extendable/retractable support attached to a side of the displaceable interface opposite to the side engaged by the breast or other tissue volume. The extendable/retractable support typically has an interior with a variable volume. In such cases the low pressure force may be connected to apply a low pressure within the interior of the extendable/retractable support in order to bias the displaceable member. Optionally, a coil spring element is disposed within the interior volume of the extendable/retractable support to axially extend the surface of the displaceable interface and apply a spring force against the tissue volume. In such cases, the vacuum applied internally to the extendable/retractable support will be sufficient to pull and elongate the tissue volume against the spring force of the coil spring.

In other embodiments of the tissue positioning system the coil spring element may itself serve as the extendable/retractable support attached to the axially displaceable interface. The spring element may comprise, for example, a coil spring which is aligned perpendicularly to the surface of the axially displaceable interface engages the tissue volume. The spring may be covered with a sleeve, shroud, or other containment structure to define a sealed interior for connection to the low pressure source to axially bias displaceable interface against the spring force to pull, elongate, and/or contour the tissue volume captured by the interface surface.

In a second aspect of the present invention, a system for scanning a breast tissue volume of the patient comprises a table or base having a horizontal surface with an opening therein. The table or base has an upper surface configured to support the patient in a prone position with a breast depending through the opening. An imaging device is disposed below the base and configured to image the breast as it depends through the opening. A vertically displaceable interface has a surface configured to engage tissue surrounding a nipple of the breast, and a low pressure source is configured to apply a low pressure to the surface of the displaceable interface. The low pressure secures the breast tissue to the interface surface, and the vertically displaceable interface is biased to pull, elongate, and contour the breast tissue, typically to "cylindricalize" the breast, while the breast tissue is secured to the interface surface.

In specific aspects, the imaging device comprises an ultrasonic transducer array, and the system further comprises a receptacle or "well" disposed beneath the opening in the horizontal surface of the base, where the receptacle or well is configured to contain water or other ultrasonically transmissive medium. The ultrasonic transducer array is located within the receptacle or well and is configured to scan breast tissue while the tissue is immersed within the water or other ultrasonically transmissive medium.

The system for scanning breast tissue typically further comprises a telescoping or other extendable/retractable support having an upper end attached to a side of the displaceable interface opposite the side engaged by the breast tissue and located within the well/receptacle. The extendable/retractable support defines an interior having a variable volume, and the low pressure source is typically connected to apply the low pressure within said interior of the support to draw and engage the breast tissue to the interface.

The breast tissue scanning system typically further comprises a coil spring element within the interior volume of the extendable/retractable support. The spring element will be expanded or lengthened to position the surface of the axially displaceable interface toward the breast tissue and will typically thereafter apply a spring force that acts against the low pressure or other biasing forces that pull the interface to elongate and cylindricalize the breast. The low pressure source is typically configured to apply a sufficient force to the interface to pull and elongate the breast tissue volume against the spring force of the coil spring element.

In exemplary embodiments, the imaging device comprises an ultrasonic ring imaging array configured to circumscribe and translate over the breast. The imaging device will typically further comprise a restrictor ring over the ultrasonic ring imaging array, where the restrictor ring circumferentially constricts the breast volume so that breast tissue does not contact the ultrasonic ring imaging array as the ring is translated over the breast. The restrictor ring may have different sizes or shapes as needed, to accommodate different tissue sizes and/or shape to be scanned.

In a third aspect of the present invention, a method for imaging a patient's breast comprises locating the patient in a prone position with the breast depending downwardly through an opening in a horizontal patient support surface of a table or other base. A surface of a vertically displaceable interface is engaged against the tissue surrounding the nipple of the breast, and a low pressure is applied to the interface surface to seal the breast to the vertically displaceable interface, and the interface is biased vertically downward to elongate and contour the breast. The breast is then imaged with a device disposed below the horizontal patient support surface while the breast remains contoured.

In specific aspects of the method, imaging comprises ultrasonic imaging and the breast is immersed in a well or other receptacle containing water or other ultrasonically transmissive medium disposed below the opening in the horizontal surface. The imaging device is typically an ultrasonic transducer ring array located within the well which circumscribes breast to effect the scanning.

The vertically displaceable interface is supported by a telescoping or other extendable/retractable support located within the well, and the support typically has an upper end attached to a lower side of the displaceable interface. The extendable/retractable support typically has an interior with a variable volume, and a low pressure source may be connected to apply low pressure within the interior of the telescoping support to draw and engage the breast tissue to the interior surface. Typically, a coil spring element within the interior volume of the extendable/retractable support biases the surface of the interface vertically towards the breast tissue prior to engagement. The low pressure source typically applies sufficient force to pull and engage the breast tissue volume against the spring force of the coil spring. Imaging typically comprises circumscribing and translating an ultrasonic ring imaging array over the breast, and the ultrasonic ring imaging array may comprise a restrictor ring which displaces the breast so that breast tissue does not contact the ultrasonic ring imaging ray as the ring is translated over the breast.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3A is a top perspective view with a portion cut-away, and FIG. 3B is a bottom perspective view with the low pressure connector segment removed.

FIG. 6A shows the tissue restrictor ring itself. FIG. 6B shows placement of the tissue restrictor ring on a ring imaging transducer relative to a telescoping support supporting the alternative gel pad and low pressure connector configuration of FIGS. 5A and 5B. FIG. 6C shows a variation of the telescoping support supporting with a shaper cup intended to more fully cylindricalize smaller breasts.

FIGS. 8A-8D are breast tomography images taken using a breast tomography system having a breast shaping device in accordance with the principles of the methods of the present invention.

DETAILED DESCRIPTION OF THE INVENTION

The following description of preferred embodiments of the invention is not intended to limit the invention to these preferred embodiments, but rather to enable any person skilled in the art to make and use this invention.

Figure 1A:
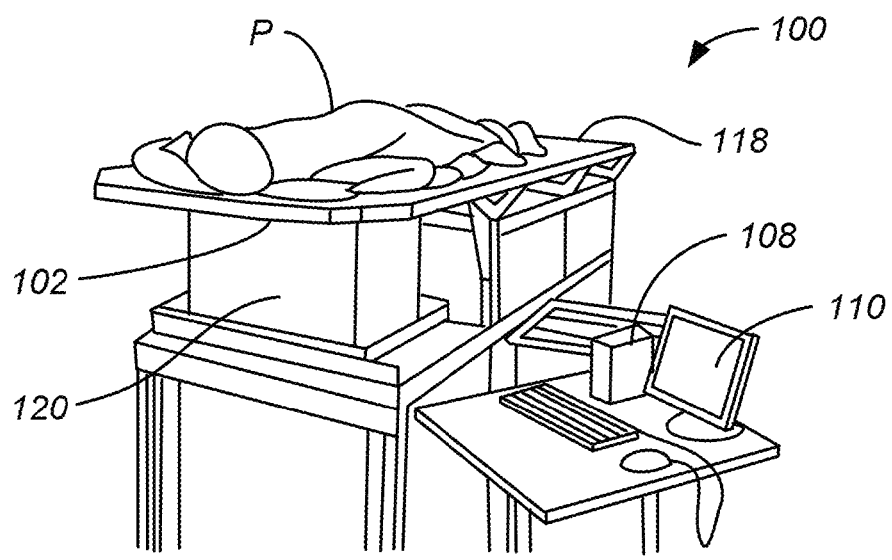
FIGS. 1A-1C illustrate a breast tomography system of the type that can employ the breast shaping device and tissue restrictor ring of the present invention.
Figure 1B:
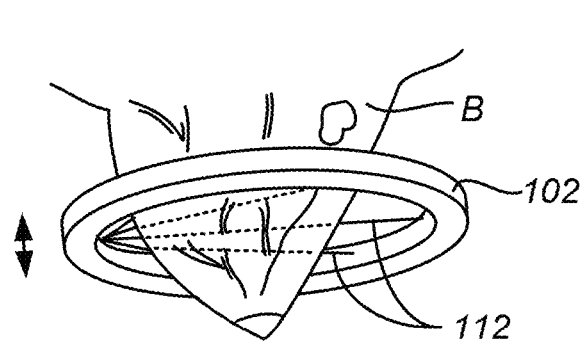
Figure 1C:
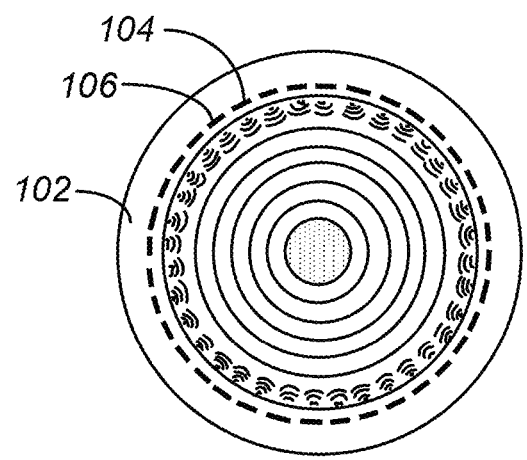

Referring to FIGS. 1A to 1C, a breast tomography system 100 of the type that can employ the breast shaping device and the tissue restrictor ring of the present invention comprises an ultrasonic imaging ring array 102 including a plurality of ultrasound emitters 102 and ultrasonic receivers 106. The ultrasonic imaging ring array 102 may be configured to surround a breast or other tissue volume so that the plurality of ultrasound emitters 102 emits acoustic waveforms 112 toward the volume of tissue. The plurality of ultrasound receivers 106 is configured to receive acoustic waveforms scattered by the volume of tissue, and a processor 108 is configured to generate a tomographic images based on the received acoustic waveforms as described in commonly owned, copending application nos. PCT/US2016/050014; Ser Nos. 14/817,470; 14/811,316; 18/703,746; 14/819,091; 14/208,181; 14/015,459; and 13/894,202, the full disclosures of which are incorporated herein by reference. The system 100 can further include a display 110 on which the acoustic data and/or generated image rendering can be displayed, such as to a medical practitioner and/or the patient. The ultrasonic imaging ring array 102 is configured to scan vertically to produce an image of the breast B which depends through an opening or aperture 116 (see FIGS. 7A-7C) in a table 118 having an upper surface for supporting patient P in a prone position. The breast is immersed in water or other ultrasonically transmissive liquid held in a reservoir enclosure 120 located beneath the table. As described in greater detail below, the breast shaping device and the tissue restrictor ring of the present invention are located within the reservoir enclosure 120.

Figure 2A:
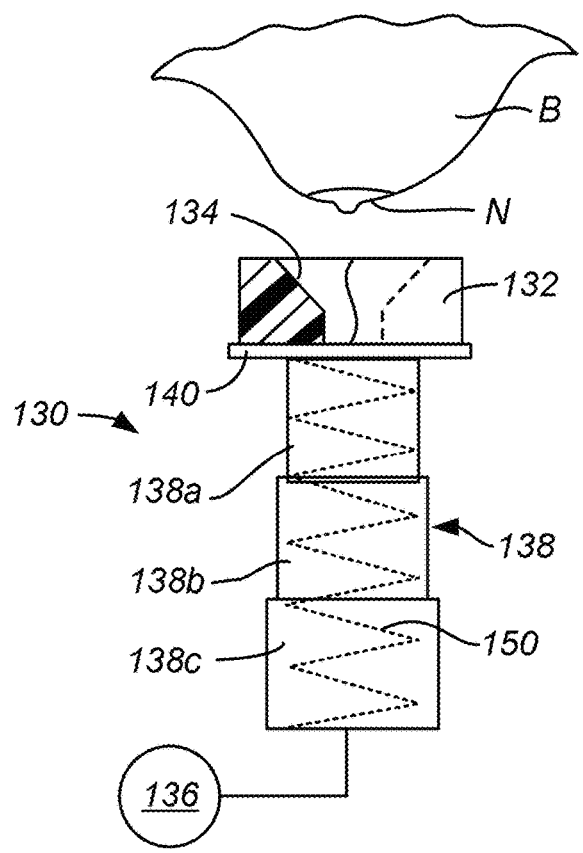
FIGS. 2A-2C illustrate a first embodiment of a breast shaping device constructed in accordance with the principles of the present invention.
Figure 2B:
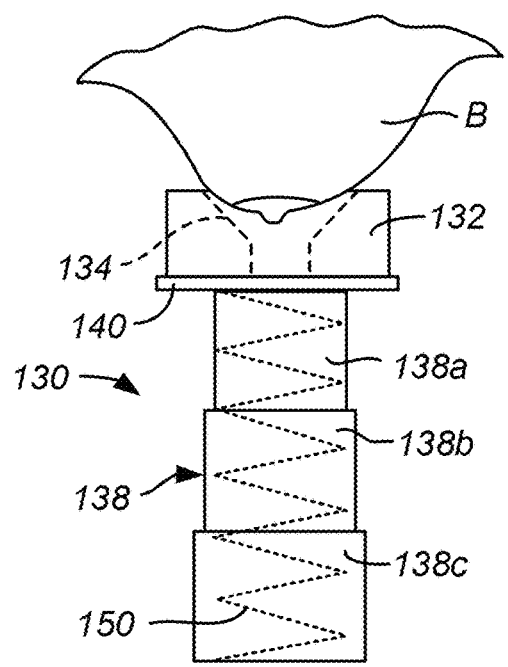
Figure 2C:
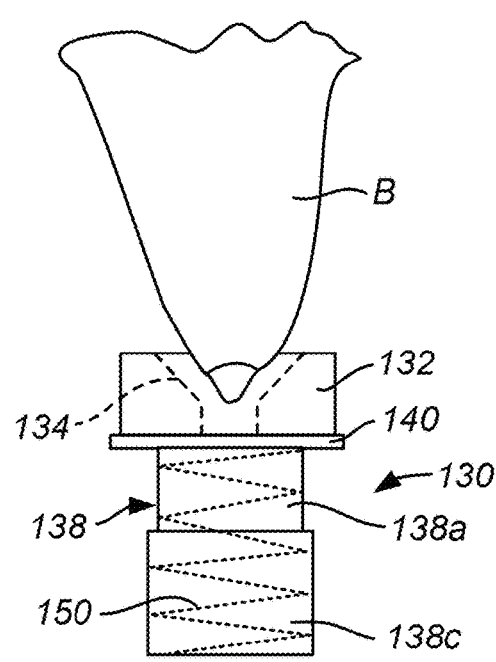

As shown in FIGS. 2A-2C, a breast or other tissue shaping device (BSD) 130 for positioning a tissue body includes a toroidal pad 132 having an opening 134 for receiving a target region on a tissue body, such as a nipple region N on a breast B. A low-pressure or "suction" source 136 is coupled to the toroidal pad 132 through an interior of, or interior passage within, an extendable/retractable supporting column 138, which is typically a telescoping column including an upper chamber or segment 138a, a middle segment 138b, and a lower segment 138c. While three segments have been found to be a useful number, it will be appreciated that as few as two or as many as five or more segments might also find use. Other non-telescoping designs, such as accordion designs, could also be employed. In all cases, however, the supporting column should be sufficiently sealed so that the low pressure source coupled to the column can be transmitted into the interior of the column and to the toroidal pad 132.

The BSD 130 functions to comfortably immobilize a breast B or other tissue body of a patient, such that the tissue body can be properly scanned e.g., for monitoring, for medical diagnostics, etc. Additionally or alternatively, the BSD 130 can pull breast or other the tissue body away from the body of the patient, e.g., the breast can be pulled away from chest wall of the patient, thereby enabling a larger percentage of the tissue body to be scanned, e.g., for lesions. The BSD 130 can additionally or alternatively function to properly position a breast or other tissue body within a scanning region of an imaging system, thereby increasing efficiency in processing of image data or other data. The BSD 130 can additionally or alternatively function to stretch the tissue body, thereby reducing a thickness of tissue structures (e.g., skin) in order to provide an improved scan of the tissue body. Finally, the BSD 130 can provide a sanitary means for positioning the tissue body, for a scanning system that is used for multiple patients.

In a specific example, the BSD 130 immobilizes a volume of breast tissue to enable scanning of smaller breasts by elongating and contouring the breast relative to the chest wall to reduce glancing angle effects in relation to incident waves on a tissue surface, enable detection of legions closer to the chest wall by pulling a higher percentage of breast tissue away from the chest wall, improving centering of the breast in a scanning region of interest to reduce computational load in post-processing of scan data, e.g., with sound speed measurements, with attenuation measurements, with reflection measurements, with time of flight measurements, with density measurements, with stiffness measurements, etc., and induce elongation (e.g., "cylindricalize") of the volume of breast tissue, thereby inducing a reduction in thickness of skin of the breast to improve scan data.

The BSD 130 is preferably configured to be used within a volume of an ultrasonically transmissive scanning medium (e.g., water) retained within the reservoir enclosure 120 of the ultrasound tomography system 100. The BSD 130 properly immobilizes the breast or other tissue body within the scanning medium so that the tissue body can be properly scanned without disturbance caused by tissue buoyancy. As such, the system can interface with embodiments, variations, and examples of one or more elements of the system for providing scanning medium described in U.S. application Ser. No. 14/811,316, entitled "System for Providing Scanning Medium" and filed on 28 Jul. 2015, which is herein incorporated in its entirety by this reference. Additionally or alternatively, the system 100 can interface with embodiments, variations, and examples of one or more elements of the patient interface system configured to support the body of a patient during a scan, as described in U.S. application Ser. No. 14/208,181, entitled "Patient Interface System" which has been previously incorporated herein by reference. However, the BSD 130 for positioning a tissue body described herein can additionally or alternatively interface with any other suitable elements/systems.

Figure 3A:
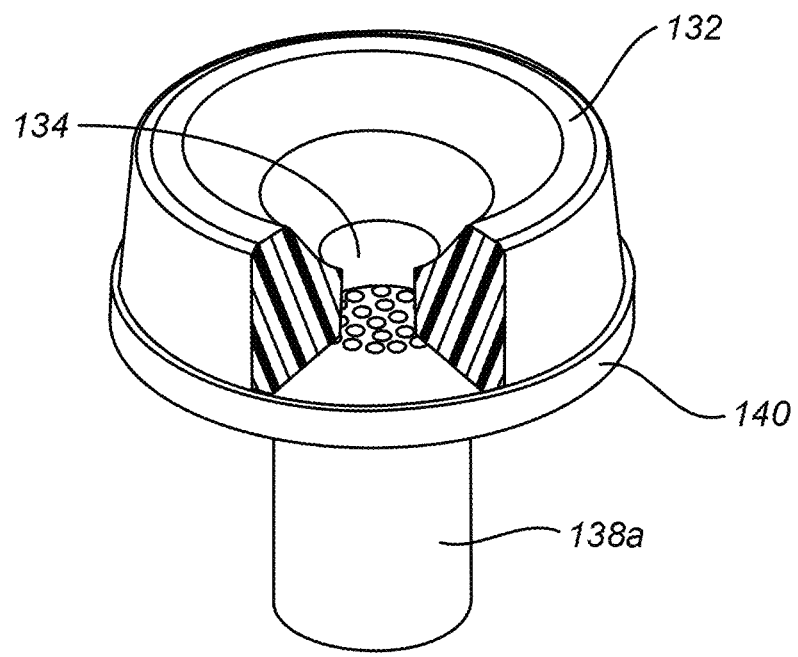
FIGS. 3A and 3B are detailed views of a gel pad and low pressure connector segment used in the breast shaping device of FIGS. 2A-2C.
Figure 3B:
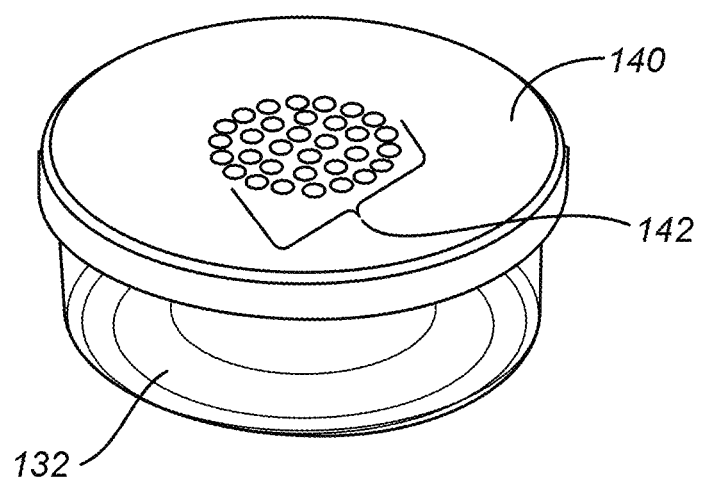

As shown in FIGS. 3A and 3B, the toroidal pad 132 is formed from a silicone rubber or similar complaint material, and a bottom surface of the toroidal pad 132 is typically attached to an interface plate 140 with a plurality of holes or perforations 142 therein. The opening 134 is configured to receive a target region of the tissue body, such as the region surrounding the nipple N of the breast B, as seen in FIGS. 1A-1C. The opening 134 will usually have a funnel or conical portion formed in the upper surface of the toroidal pad 132 and functions to comfortably receive ad attach the tissue body during a scan.

While preferably toroidal, the pad 132 could have other, non-toroidal geometries, such as ovoid, polygonal, and the like. The pad 132 will have a thickness, a top surface, a bottom surface, and opening 134 through the thickness that allows negative pressure to be transmitted to tissue engaged against the top surface and/or received within the opening. Preferably, the dimensions of the pad 132 (in combination with the material properties) provide a pad with a suitable buoyant behavior for scanning applications in a scanning medium used. For instance, the pad 132 can be configured such that it does not float in scanning medium in an undesired manner. In one variation, the footprint of the pad 132 is circular; however, the footprint can alternatively have any other suitable shape (e.g., ellipsoidal, rectangular, polygonal, amorphous, etc.). In one variation, the top surface is approximately frustoconical (e.g., shaped as an inverted funnel) in order to comfortably support a portion of the tissue body. The top surface can alternatively have any other suitable profile (e.g., a profile that is complementary to or matched to a specific tissue body). In another variation, the top surface is substantially planar (although a slight degree of convexity or concavity is acceptable) with low pressure plenums about the periphery. The shape of the bottom surface is less critical, usually being substantially planar; however, in alternative variations, the bottom surface can have any other suitable profile. In one variation, an opening in the bottom surface to connect the low pressure sources is circular and centrally located (e.g., concentric with the inverted funnel of the top surface or configured to branch into plenums about the periphery of the top surface); however, in alternative variations, the opening can alternatively have any other suitable cross section (e.g., ellipsoidal, rectangular, polygonal, amorphous, etc.) and/or be non-centrally located relative to the top surface of the pad 132. Furthermore, the pad 132 and/or the opening may not have constant cross sections through the thickness of the pad 132. For instance, the pad 132 can taper in profile from its bottom surface to its top surface, and/or the opening can have a different cross section at the bottom surface in comparison to the cross section of the opening at the top surface, in order to accommodate the reference region of the tissue body and enable immobilization of the tissue body comfortably, by way of the negative pressure generated by the low pressure subsystem 136.

In specific examples, the pad 132 has a cylindrical outer surface and has an outer diameter from 0.5 cm to 3 cm; the top surface is an inverted frustoconical surface having a base angle from 5° to 85°, the thickness of the pad is from 1 cm to 5 cm, the bottom surface is substantially planar, and the opening is a circular opening through the thickness of the pad, with a constant cross section having a diameter from 0.5 cm to 3 cm. While one opening is described above, the pad 132 can alternatively have multiple openings in order to immobilize the tissue body at multiple points on the surface of the tissue body. In specific examples, the pad 132 is preferably configured as a "one-size-fits-all" element that accommodates a wide variety of breast morphologies; however, the pad 132 can additionally or alternatively be customized to the morphology of each patient being scanned.

In relation to the top surface and the opening, the reference or target region of the tissue body is preferably a most extreme region of the tissue body (e.g. a region that protrudes or otherwise provides an attachment location such as a nipple on a breast), in the orientation in which the patient interfaces with the pad 132. In the context of a volume of breast tissue, the reference region can be a most-anterior region of the breast (e.g., the nipple region), such that the nipple region of the breast is retained at the opening of the pad 132 to properly immobilize the breast of a patient who is in a prone position. However, the target or reference region can additionally or alternatively be any other suitable region of a tissue body that facilitates immobilization of the tissue body.

The pad 132 is preferably composed of a material having a high degree of acoustic transparency, such that the pad does not interfere with proper scanning of regions of the tissue body within the pad 132. As such, in some variations, the material composition of the pad 132 can thus provide closer focusing at the interface between the tissue body and the pad 132 (e.g., in ultrasound imaging applications). In variations, the pad 132 is composed of a polymeric material (e.g., plastic, hydrogel, etc.), and in specific examples can include a material composed of one or more of: agar, guar bean, and carrageenan; however, the pad 132 can additionally or alternatively comprise any other suitable material (e.g., natural material, synthetic material). For instance, the pad 132 can be composed of a synthetic polymer (e.g., polyurethane) processed to have desired acoustic or other characteristics. The material is preferably substantially stiff, but compliant in supporting the tissue body comfortably; however, the material can alternatively have any other suitable properties (e.g., hardness, stiffness, porosity, transparency, thermal characteristics, optical characteristics, electrical conductivity characteristics, rheological characteristics, etc.). Furthermore, the pad 132 can be configured for single-use applications (e.g., to provide a sanitary option) and/or can be configured to controllably degrade (e.g., in a manner that does not affect fluid handling components of the scanning system) after a certain number of uses in order to prevent repeated uses of the pad 132. However, the pad 132 can alternatively be configured to be reusable. In a specific example, the pad can comprise a blend of agar, guar bean, and carrageenan, and be configured to have a specific gravity of 1.06 (e.g., slightly heavier than water); however, the pad 132 can have any other suitable composition.

The interface plate 140 functions to allow the pad 132 to be properly seated at a receiving portion of a low pressure system as described below. In more detail, the interface plate can allow the pad 132 and the opening 134 of the pad 132 to be properly aligned and positioned in relation to the segments 138a, 138b, and 138c of the support column 138 for transmission of a low pressure from source 136, thereby allowing the target region of the tissue body to be drawn into the opening of the pad 132.

Figure 4A:
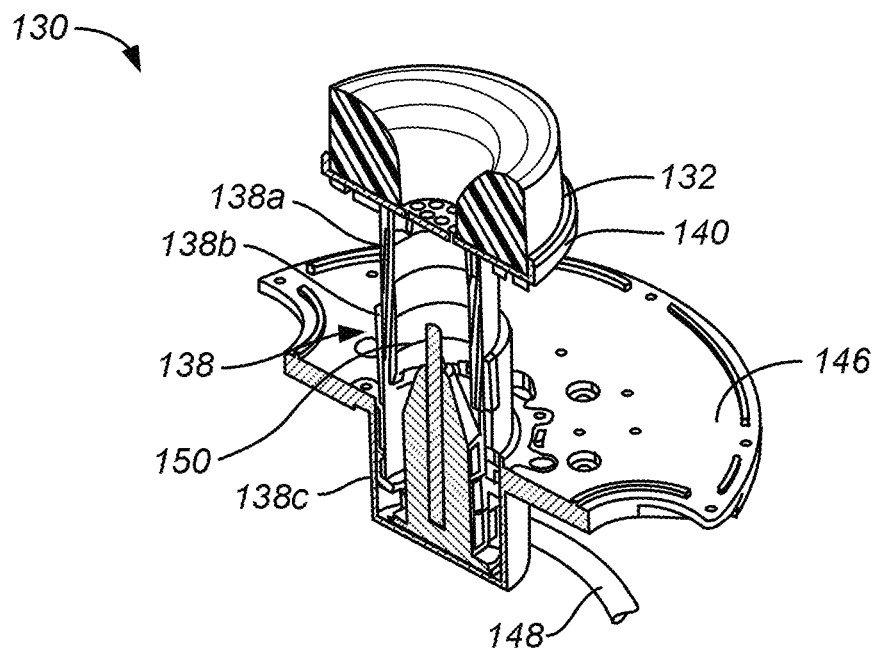
FIGS. 4A and 4B are detailed views of a telescoping support for the gel pad and low pressure connector used in the breast shaping device if FIGS. 2A-2C, shown in a vertically extended configuration in FIG. 4A and vertically retracted configuration in FIG. 4B.
Figure 4B:
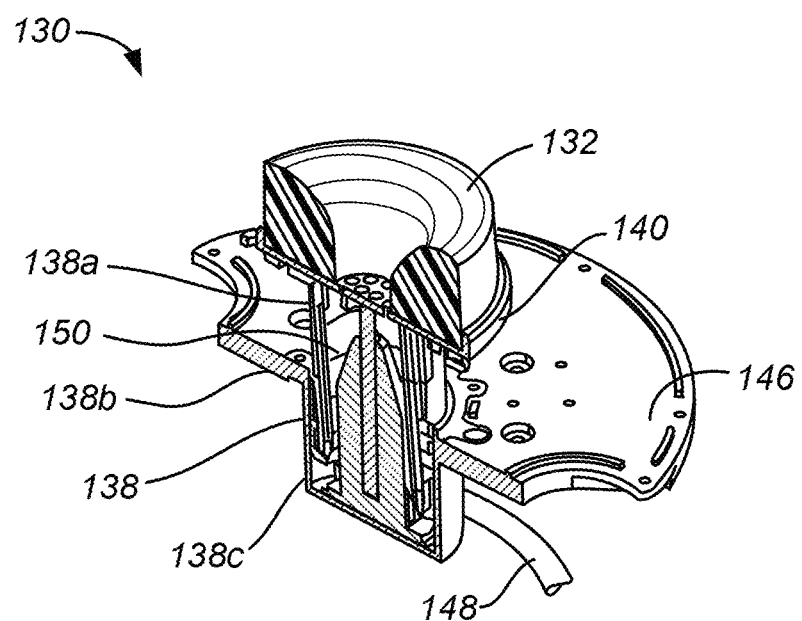

Referring to FIGS. 4A and 4B, the lower segment 138c of the extendable/retractable support column 138 of the BSD 130 is mounted on or through a bottom plate 146 of the reservoir enclosure 120 of the tomography system 100. The lower segment 138c is connected to the low pressure source 136 (FIG. 2A) by a connector 148. The middle segment 138b of the extendable/retractable support column 138 is translatable relative to the lower segment 138a, and the upper segment 138c is translatable relative to the middle segment 138b. During operation, the toroidal pad 132 preferably translates with the upper segment 138a to a position that comfortably engages the tissue body, and the target region of the tissue body is preferably retained at the opening 134 of the toroidal pad 132 by way of the negative pressure generated by the low pressure system 136, such that the tissue body is properly immobilized during scanning (e.g., using a tomography system). The low pressure system 136 thus functions to both (1) generate the negative pressure for retaining the tissue body in position and (2) comfortably support the tissue body at an appropriate position during scanning.

The segments 138a, 138b, and 138c of the column support 138 are preferably substantially cylindrical, having a wall with an appropriate thickness and a longitudinal axis that is parallel to and concentrically aligned with the opening 134 of the pad 132 in assembled system. Furthermore, the upper segment 138a is preferably oriented vertically, such that the support column 138 can properly immobilize a tissue body (e.g., volume of breast tissue) for a patient who is interfacing with the BSD 130 in a prone position. However, in alternative variations, the segments 138a, 13b, and 138c can have any other suitable shapes (e.g., non-cylindrical, polygonal, prismatic, etc.) and/or orientation that provides proper relative motion between the segments.

The column 138 including segments 138a, 138b, and 138c can be composed of a polymeric material (e.g., a plastic), a metallic material, a composite material, a ceramic material, a glass, and/or any other suitable material. Some or all of the segments 138a, 138b, and 138c are preferably configured to support the negative pressures and/or positive pressures implemented in the BSD 130 without deformation. The segments, however, can alternatively have any other suitable composition and/or be configured with any other suitable mechanical properties. In some cases, one or more of the segments 138a, 138b, and 138c can include stops configured to define limits of the relative range of motion of the segments. Additionally or alternatively, the expansion range of the segments can be defined in any other suitable manner, as described in more detail below.

The lower segment 138c preferably has a base region and a superior region, wherein the base region is coupled to the base plate 146 of a imaging tank in the reservoir enclosure 120 associated with the tomography system 100, and the superior region is open to interface with the middle segment 138b and upper segment 138a. Preferably, the low pressure source 136 connects with the lower segment 138c via the connector 148 near the base, but the low pressure source 136 can additionally or alternatively interface with any of the segments at any level in the column. Still alternatively, the low pressure source 136 can interface with an internal portion of the supporting column 138 or can be connected to the opening 134 in the pad 132 by a separate conduit.

Preferably, the low pressure source 136 can generate a negative pressure of up to approximately 200 mmHg in order to retain the tissue body in a comfortable manner (and as regulated by the U.S. Food and Drug Administration, in some embodiments). In one variation, the low pressure source can provide a negative pressure over a range that includes the range between 100 and 125 mmHg, which, in a specific embodiment, can properly immobilize the tissue body without causing discomfort. However, the low pressure source 136 can alternatively generate pressures over any other suitable range, and can be configured to generate negative pressures and/or positive pressures. Furthermore, the low pressure source 136 can be configured to generate appropriate pressures during different phases of scanning (e.g., in relation to patient preparation, initialization, mid-scan, scan completion, etc.).

For instance, in some variations, the low pressure source 136 can provide a higher negative pressure (e.g., 125 mmHg) during initialization phases when the tissue body of the patient is first being immobilized; however, once the tissue body is properly immobilized and scanning initiates, the pressure value can be reduced (e.g., to 50 mmHg), thereby increasing comfort while still allowing the tissue body to be effectively retained in position. Finally, when scanning is completed, the negative pressure can be eliminated, or even reversed (e.g., to expel the tissue body from the low pressure subsystem). In relation to varying the low pressure during operation of the system, the low pressure established by the low pressure source 136 can be adjusted manually (e.g., using an external control module). However, the pressure established by the low pressure source 136 additionally or alternatively can be adjusted automatically (e.g., by using pressure sensors that enable coordination between the low pressure source 136 and phases of scanning established by related systems, by using a mechanism that automatically reduces or increases pressure during scanning phases as described in more detail below, etc.).

The low pressure source 136 can be controlled with any suitable controller and, as such, can have an associated safety mechanism such that a maximum pressure value is never exceeded. In a specific example, the maximum pressure can be 200 mmHg; however, in alternative variations, the maximum pressure can be any other suitable pressure value. The low pressure source 136 can additionally or alternatively include a manual shutoff valve and/or any other suitable shutoff system.

The column segments 138a, 138b, and 138c are configured to be translatable relative to each other in a telescoping manner and the contiguous interiors of the segments coupled the opening 134 of the pad 132 to the low pressure source 136. In some variations, the telescoping structure can also function as a portion of a mechanism that automatically adjusts low pressures provided by the low pressure source 136, during different phases of scanning/patient orientation relative to the system. The segments 138a, 138b, and 138c are preferably configured to form a sufficiently tight sliding fit such that the interface between the segments prevents a significant low pressure leak from occurring, while still allowing sliding motion between the first and the second chambers 130, 140 to occur.

Preferably, the segments 138a, 138b, and 138c are concentrically aligned, such that each segment can provide a telescoping mechanism that allows the tissue body to be properly supported, at the appropriate depth within the scanning tank during scanning.

In one variation, the support column 138 includes a coil spring 150 which is in extension and which pushes the segments 138a, 138b, and 138c apart so that the column is in its fully extended configuration, as shown in FIGS. 2A and 4A. The spring 150 also serves to smooth out oscillations resulting from floatation of the pad 132 in water or other ultrasonically transmissive medium. The spring 150 can also provide an appropriate counterforce to facilitate proper latching of the pad 132 to the coupling interface 150 and/or of the tissue body to the pad 132. In smoothing out oscillations, the spring 150 can thus contribute to mass-spring-damper behavior of the low pressure subsystem 136 in interfacing with the tissue volume. In variations, the spring has a spring constant from 0.5 to 10 N/cm; however, the spring 150 can alternatively have any other suitable spring constant. As such, in relation to dynamically supporting the tissue body at a suitable depth within the scanning tank, the spring can allow the segments 138a, 138b, and 138c to passively provide support, while reducing oscillations when the breast or other tissue body interfaces with the pad 132, until the tissue body reaches a natural resting state within the scanning tank.

In similar, but alternative variations, the spring can be replaced with magnetic elements, wherein opposing polarities of the magnetic elements can provide spring-like behavior between the column segments 138a, 138b, and 138c. Still alternatively, the segments 138a, 138b, and 138c can be configured to translate relative to each other with the assistance of an actuator (e.g., a hydraulic actuator, a linear actuator, etc.) that allows the first and the support column 138 to have expanded and contracted configurations. The support column can alternatively be configured to have expanded and contractions in any other suitable manner.

As mentioned above, in some variations, the segments 138a, 138b, and 13c can also function as a portion of a mechanism that automatically adjusts low pressures provided by the low pressure source 136, during different phases of scanning/patient orientation relative to the system. In one such variation, the middle segment 138b its down stroke, can include appropriate cutout portions that cut off the inlet of the low pressure source 136 into the first chamber 130, thereby automatically reducing the negative pressure as the tissue body settles into the position in which it is immobilized. Additionally or alternatively, in another variation, motion of one segment relative to another segment can open and/or close a valve associated with the low pressure source 136, in order to modulate pressure. Other variations of modulating pressure can, however, operate in any other suitable manner.

In variations, the pad 132 can translate with the upper segment 138a as low pressure generated within the column retracts the column and pulls down the target region of the tissue body, such as the nipple region N of the breast B, as shown in FIG. 2B (where the nipple is first attached, reducing pressure within the column) and FIG. 2C where the breast is pulled down to a position that comfortably supports the tissue body for scanning. For breast scanning, this pulling cylindricalizes the volume of breast tissue, and draws breast tissue away from the chest wall, such that the tissue body is properly immobilized during scanning (e.g., using a tomography system).

Figure 5A:
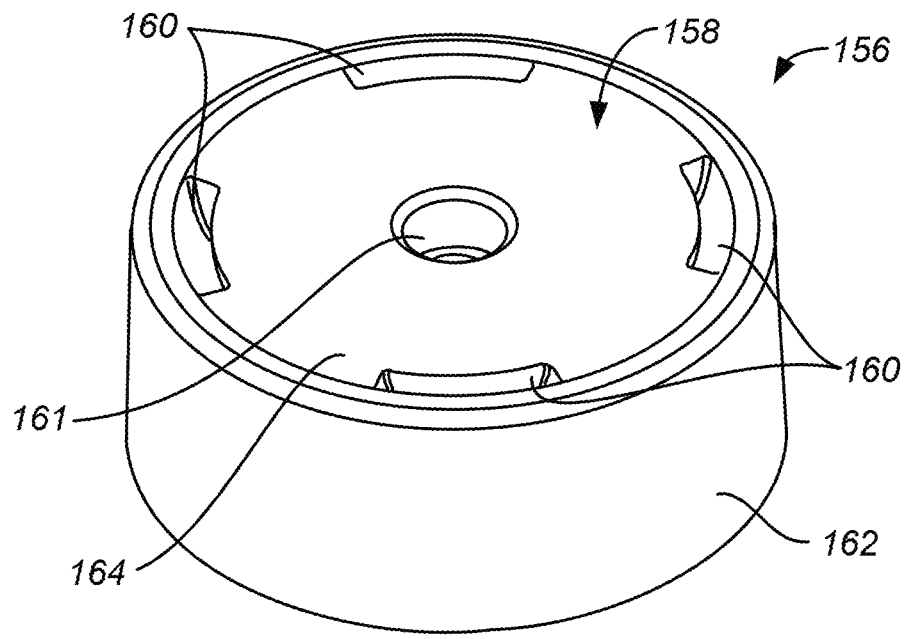
FIGS. 5A and 5B illustrate an alternative gel pad and low pressure connector configuration having a flat upper surface to enhance cylindrical shaping of the breast.
Figure 5B:
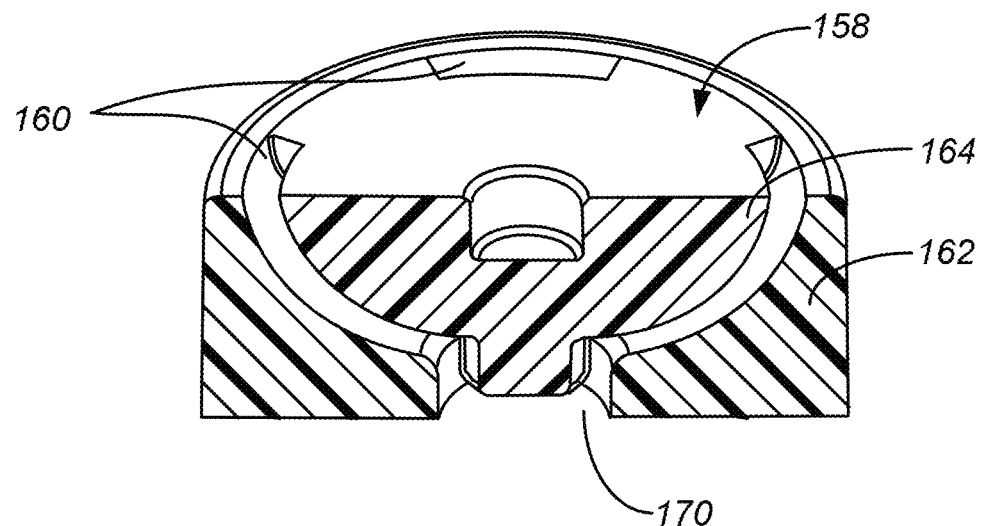

Referring now to FIGS. 5A and 5B, an alternative interface pad 156 has a flat or planar upper surface 158 which is typically circular with a single hole 161 in the center of the surface. The hole is intended to accommodate a patient's breast nipple as will be described in detail below. In contrast to toroidal pad 132 described previously which draws the low pressure through a central passage, the interface pad 156 has four annularly placed peripheral plenums 160 to distribute a low pressure about the surface's periphery. This arrangement allows a larger target region surrounding the patient's nipple to be secured to the flat surface which in turn improves the cylindricalization of the breast. The peripheral plenums provide improved attached to the peri-areolar region of the breast. In contrast, the smaller low pressure funnel of toroidal pad 132 will shape the breast in a more conical configuration which may be less desirable for overall breast imaging. In some instances, however, the conical breast presentation may allow better visualization of the sub-areolar regions for masses underlying the nipple, e.g., to detect papillomas and other cancerous lesions.

As best seen in FIG. 5B, each of the peripheral plenums 160 is connected to a lower opening 170 by curved connecting channels which are formed in between an outer shell 162 and a dome-shaped insert 164. The interface 156 may thus be molded from any of the polymers described previously in a simple, two-part molding process where the outer shell 162 and insert 164 may thereafter be joined by adhesives, ultrasonic welding, or other conventional techniques. Interface pad 156 may be connected to an expandable/retractable column 138 in the same manner as was described for toroidal pad 132.

Figure 6A:
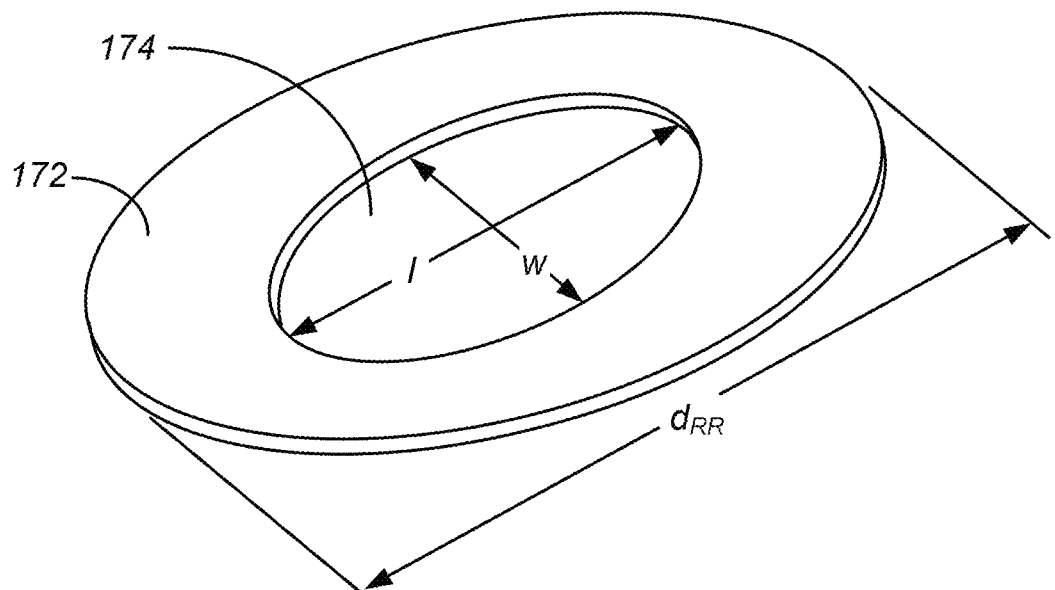
FIGS. 6A-6C illustrate a tissue restrictor ring constructed in accordance with the principles of the present invention.
Figure 6B:
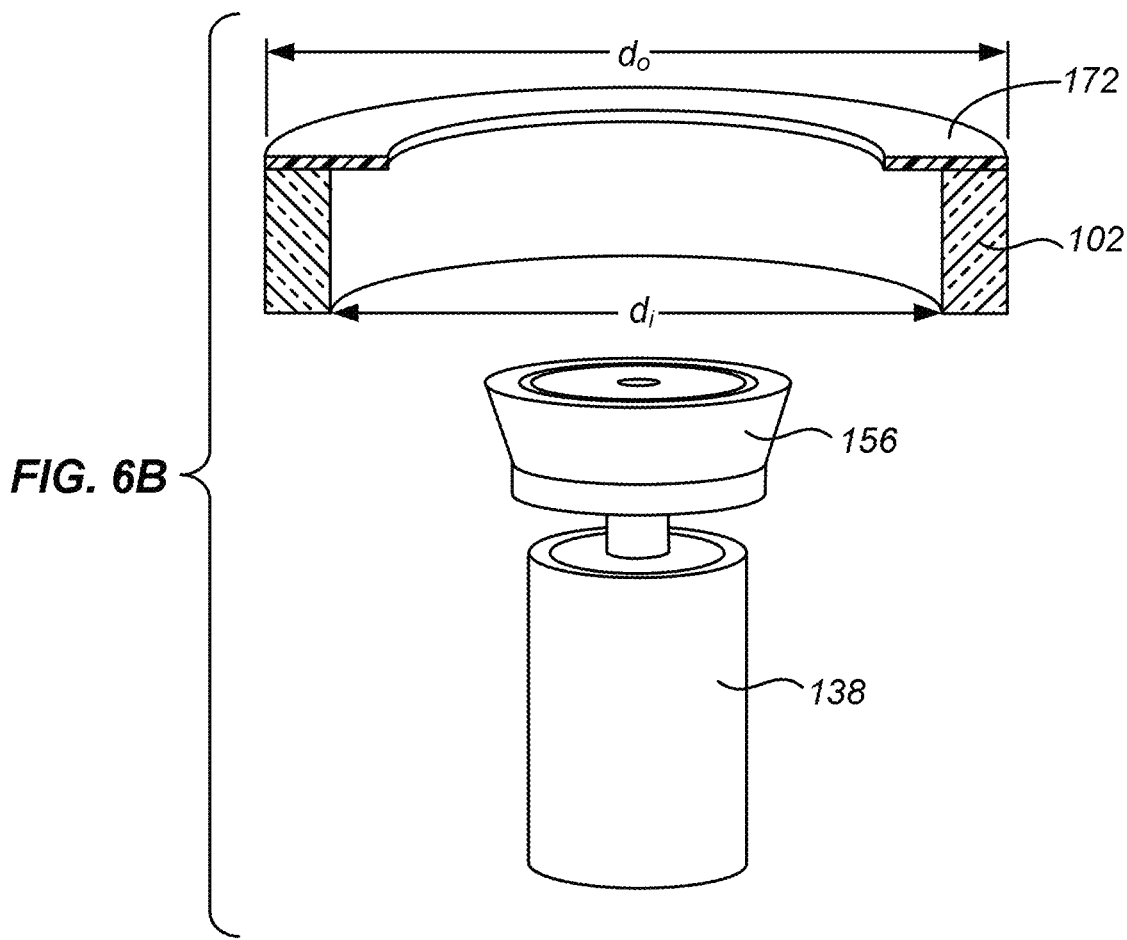

Referring now to FIGS. 6A and 6B, a restrictor ring or plate 172 may be placed over and attached to the ultrasonic ring imaging array 102 in order to displace breast tissue as the transducer is vertically scanned over the breast, as will be described in greater detail below. The restrictor ring 172 will have an inner aperture or opening 174 which has dimensions which are smaller than those of the inside of the imaging array 102, thus creating an "overhang" or "offset" to push tissue away from the active inner surface of the array. Typically, the restrictor ring 172 will provide an overhang of at least 1 cm, and typical dimensions for both the restrictor ring and the imaging array are set forth in Table 1 below.

TABLE 1

|  | BROAD RANGE (cm) | SPECIFIC RANGE (cm) |
| --- | --- | --- |
| $d_{RR}$ | 25-30 | ~27 |
| l | 12-22 | 16-20 |

TABLE 1-continued

|  | BROAD RANGE (cm) | SPECIFIC RANGE (cm) |
| --- | --- | --- |
| w | 10-22 | 12-20 |
| $d_o$ | 25-30 | ~27 |
| di | 20-25 | ~22 |

The restrictor ring 172 will be relatively stiff so that it will not bend or deform when engaging the breast tissue. It will also typically have a relatively thin profile, usually being from 2 to 3 mm thick, to minimize any deleterious effect on imaging. In some cases, the restrictor ring 172 may be made from materials, such as Delrin® polymer, to reduce out-of-plane scattering. The interior opening 174 of the ring 172 may be circular but in many embodiments will be ovoid or tear-shaped with the typical dimensions given in Table 1. Tomography systems 100 may be provided with an inventory of differently sized restrictor plates 172 corresponding to different breast sizes. In this way, an imaging system can be optimized for many women with differing anatomies.

Figure 6C:
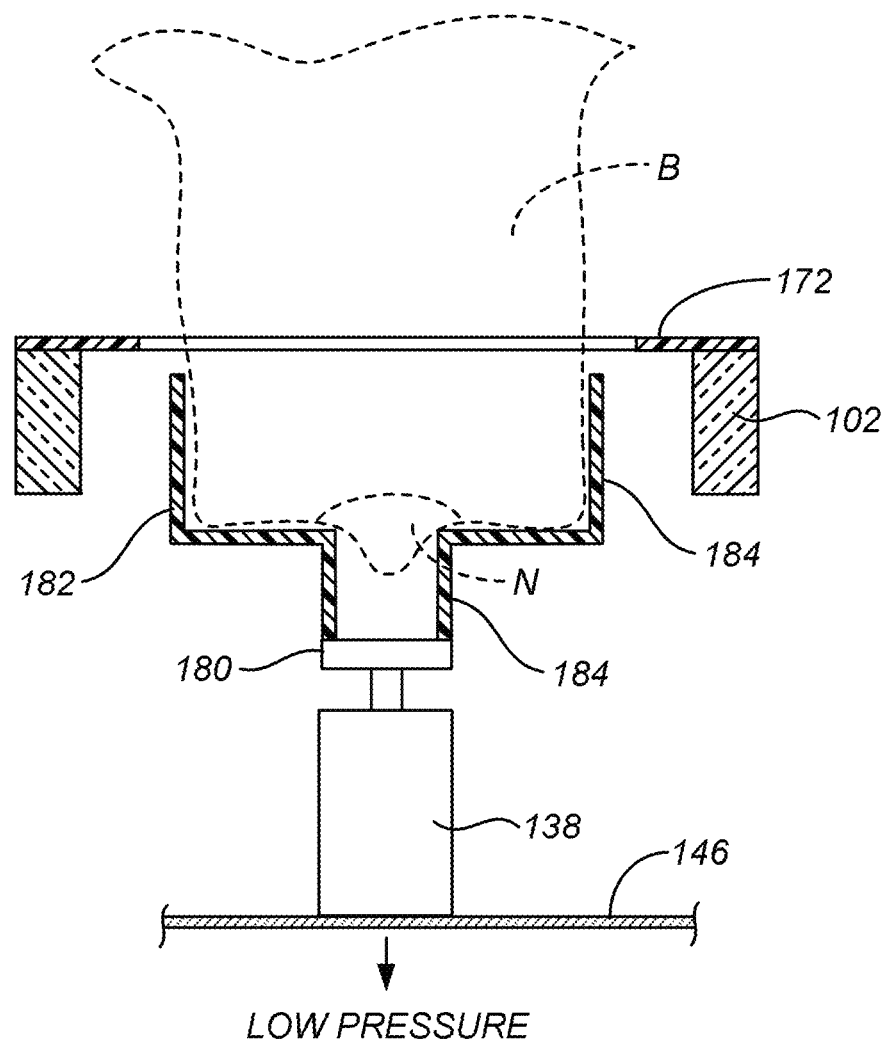

FIG. 6C shows an alternative breast shaper concept where a cylindrical cup 182 is secured to an upper surface of a connector disc 180 which in turn is supported on an extendable/retractable support column 138. The shaper cup 182 may have particular benefit for women with smaller volume breast tissue (e.g., cup size A), whereby even a restrictor ring 172 with the smallest inner diameter (w) and the peripheral suction alternative gel pad (FIG. 5A/B) would still lead to a conical overall transition from the chest wall to the peri-areolar region. Therefore, shaper cup 182 could virtually encircle nearly all breast tissue of a smaller breast, engage the entire breast with the gentle suction and elongate the breast upon retraction, while providing near-complete cylindricalization of all available breast tissue. This embodiment could also be envisioned for larger breasts as needed. The shaper cup 182 includes an upper portion 184 having a diameter in the range from 10 cm to 20 cm, where the dimensions of the ultrasonic ring imaging array 102 and the restrictor ring 172 are generally in the ranges set forth in Table 1. A smaller transition region 186 is connected directly to the connector disc 180 so that low pressure induced in the column 138, typically by a recirculating water or other media flow, is transferred to an interior of the upper portion 184. In this way, the region of the breast B surrounding the nipple N can be drawn into the upper portion 184 where the walls of the cup 182 will cylindricalize the breast for optimized imaging, intervention, and the like. The cup 182 will preferably be formed from an ultrasonically transparent material when ultrasonic imaging is being used.

Figure 7A:
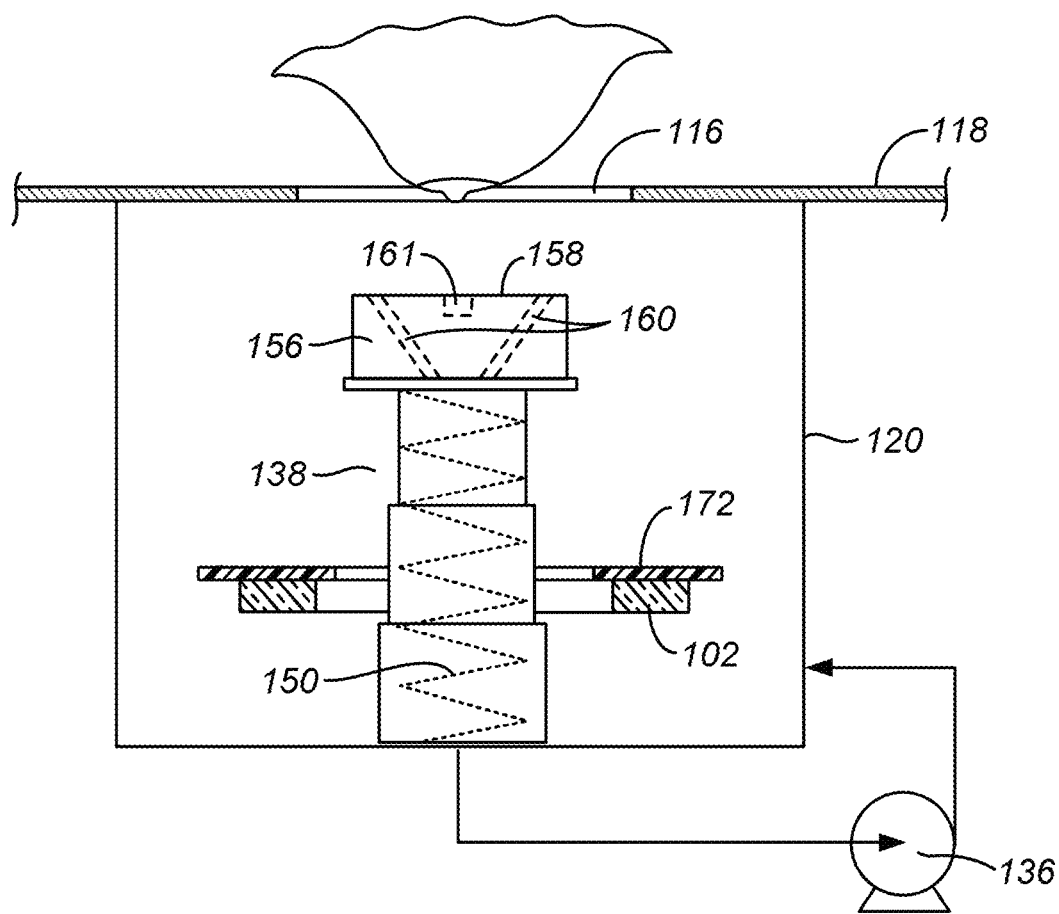
FIGS. 7A-7G illustrate the steps of using an assembly of the tissue restrictor ring, ring imaging transducer, and improved breast shaping outcome with alternate gel pad of FIGS. 6A and 6B in a breast tomography system of the type shown in FIGS. 1A-1C to image a breast.
Figure 7B:
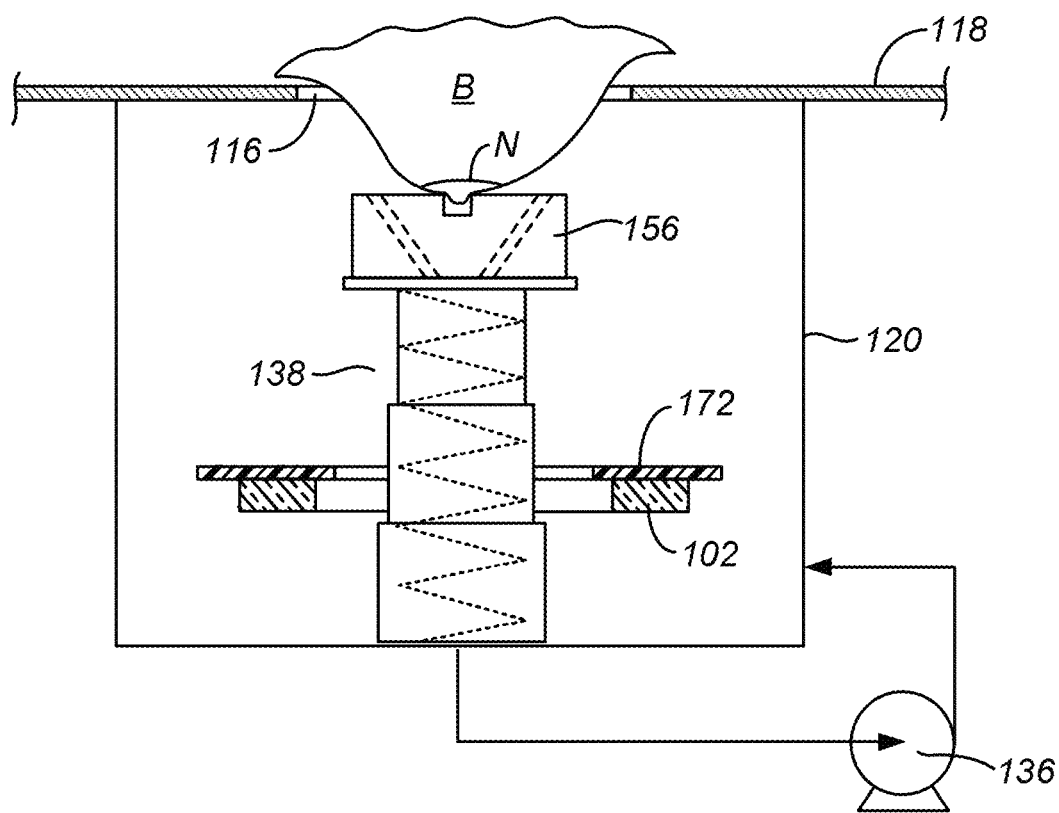
Figure 7C:
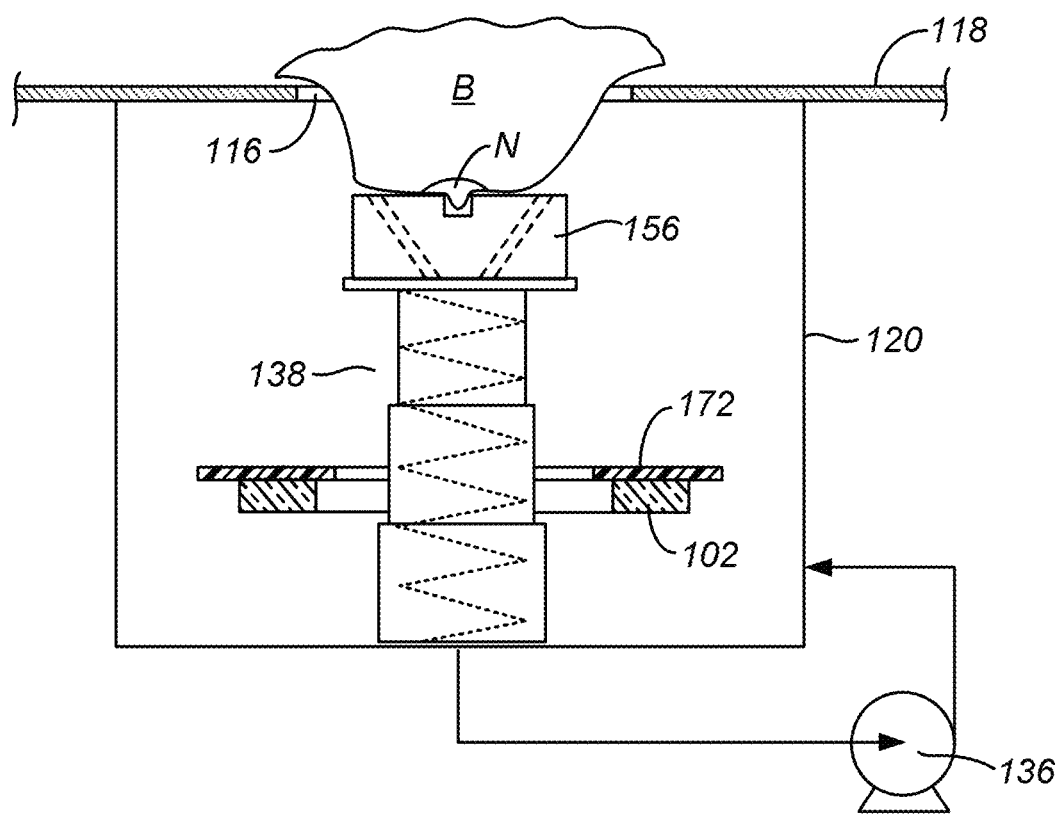

Referring now to FIG. 7A through 7G, a breast tomography system employing both the tissue shaping device and the breast restrictor ring of the present invention will be described. As shown in FIG. 7A, the interface pad 156 is initially supported on the column 138 in its vertically extended position maintained by the spring force of coil spring 150. A low pressure is maintained in the interior of support column by a circulating fluid flow 138 maintained by a pump 136 which draws the water or other ultrasonically transmissive medium downwardly through the peripheral plenums 160. As the patient lowers her breast B through the opening 116 in the table 118, as shown in FIG. 7B, the nipple N is received in the center hole 161 of the flat upper surface 158. As the patient continues to lower her breast, the breast tissue is drawn against the flat surface by the reduced pressure created by the fluid flying through the peripheral plenums 160 until the front region of the breast surrounding the nipple N is flattened against the flat surface 158 of interface pad 156, as shown in FIG. 7C.

Figure 7D:
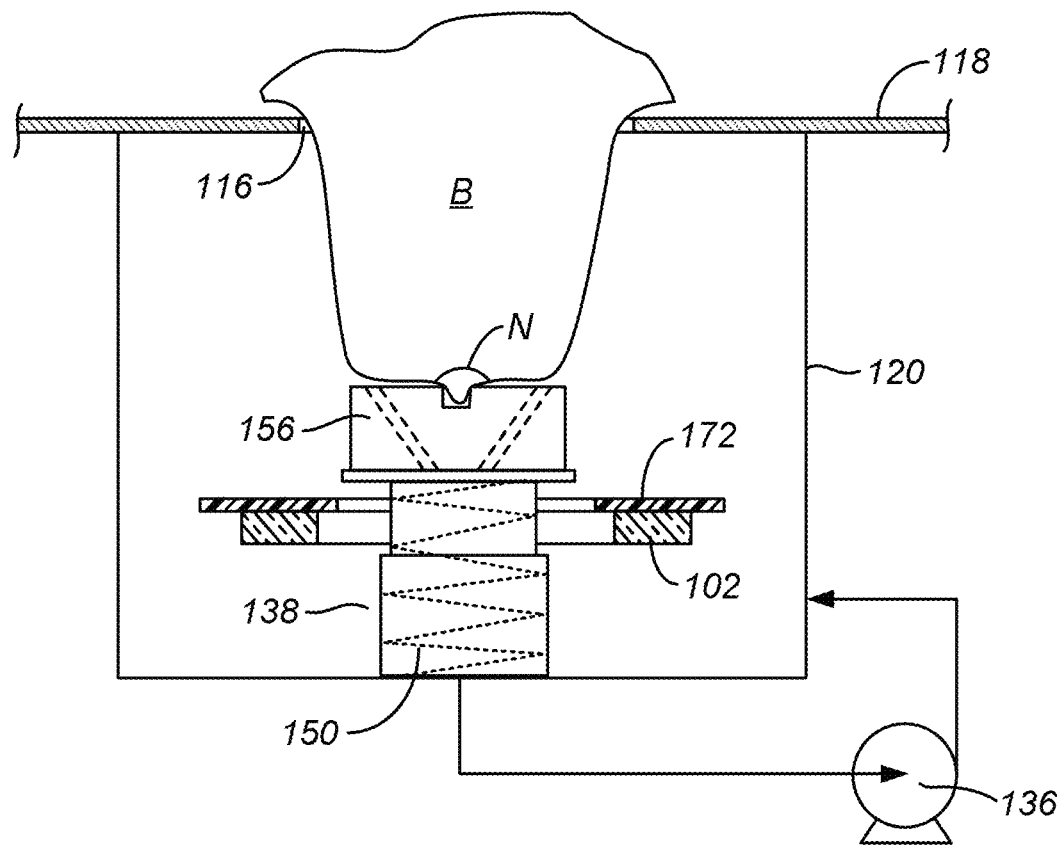

Once the breast B is flattened against the flat surface 158 of the interface pad 156, the pressure within the interior of the support column 138 will be lowered, causing a force which acts against spring 150 which causes the column to vertically retract or collapse, as shown in FIG. 7D. The force supplied by the pump 136 against the breast B can be controlled in many ways, and the breast will be lowered and elongated by an amount proper to optimize imaging, as shown in FIG. 7D.

Figure 7E:
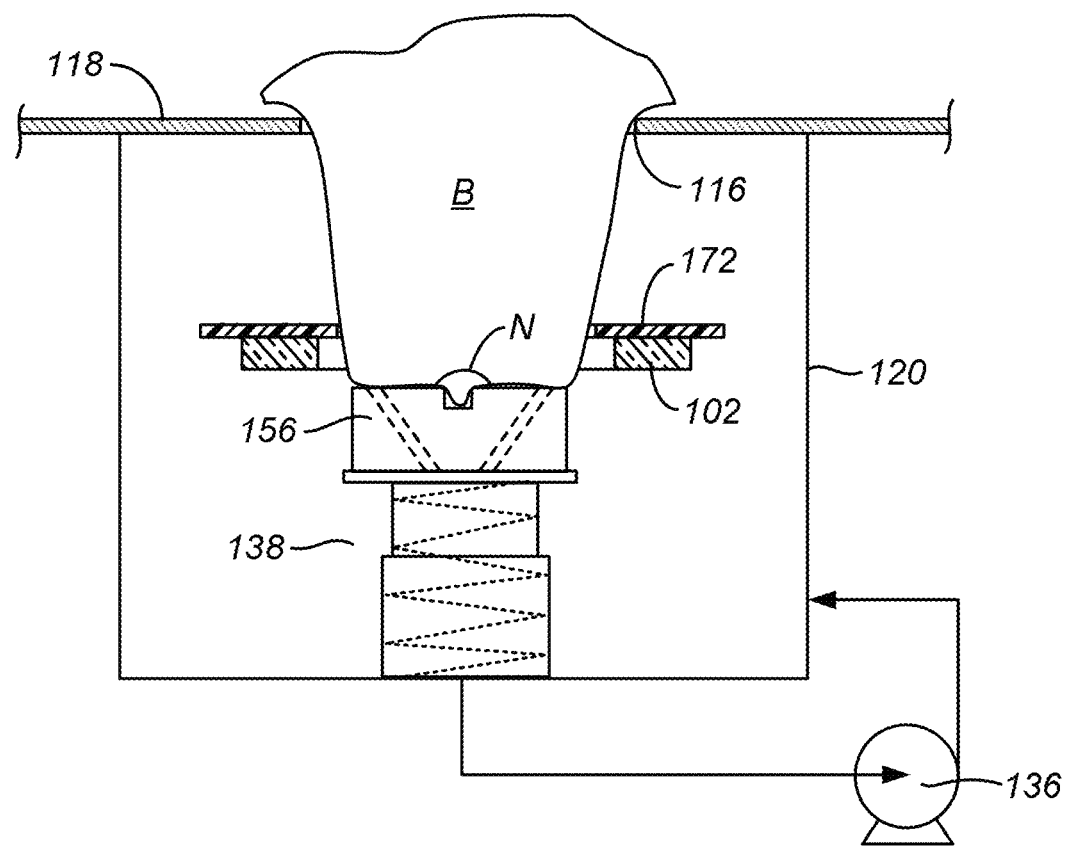
Figure 7F:
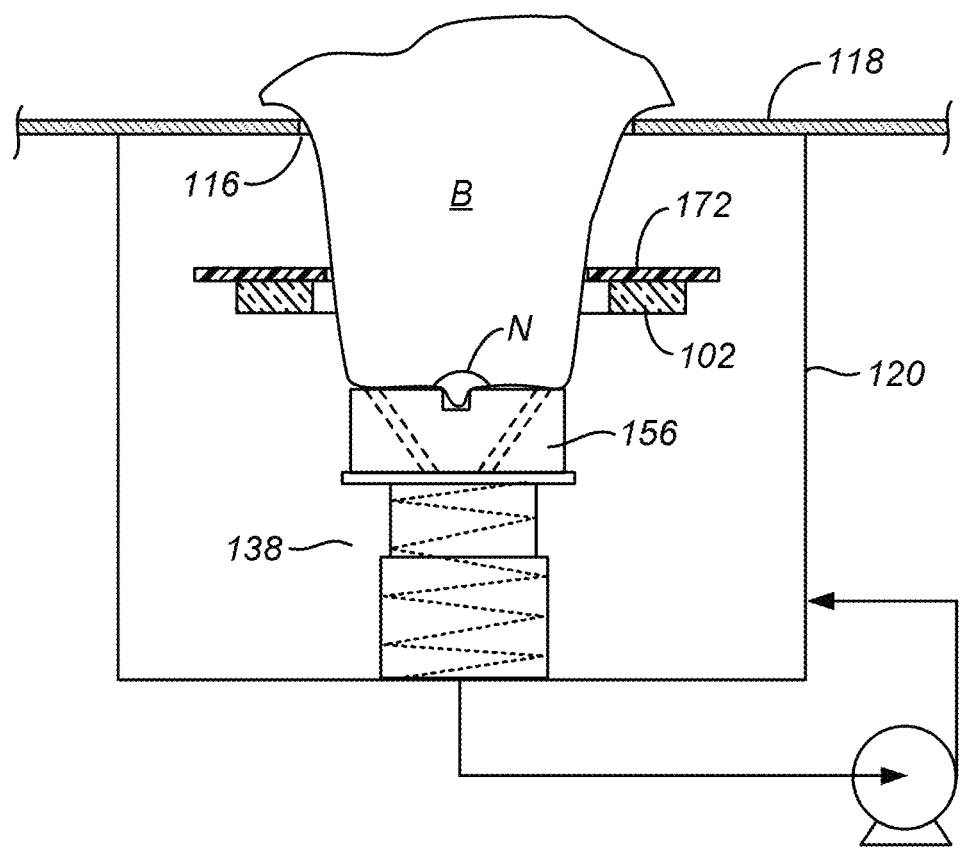
Figure 7G:
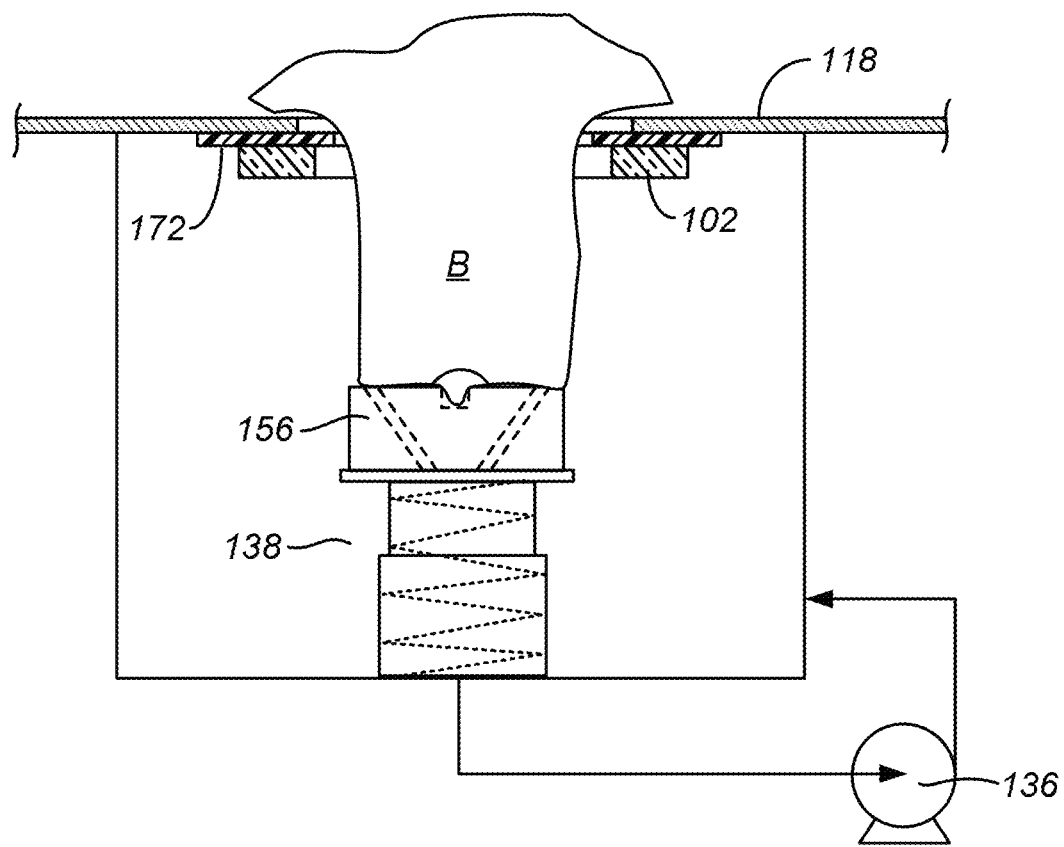
Figure 8C:
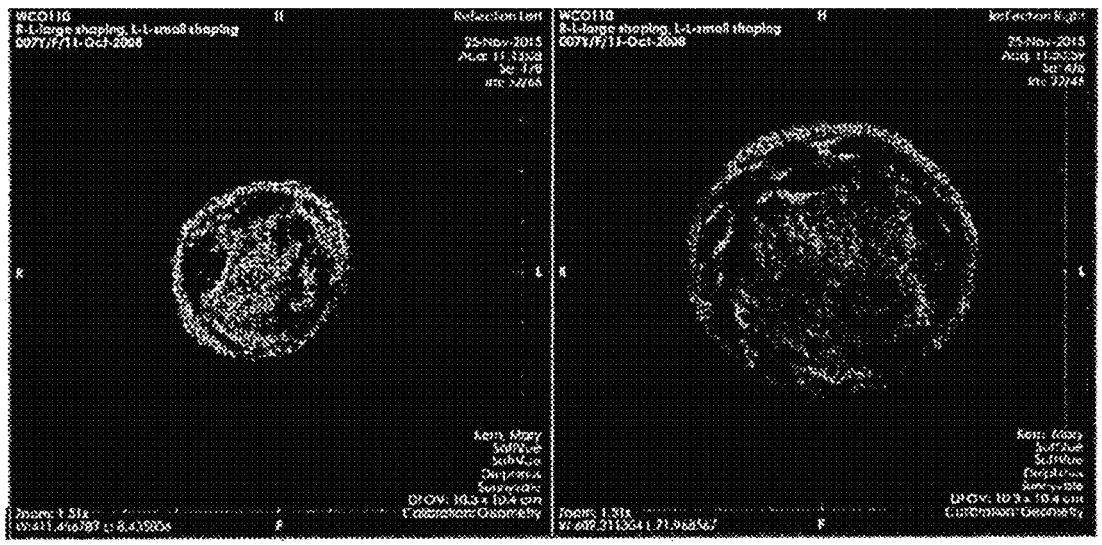
Figure 8D:
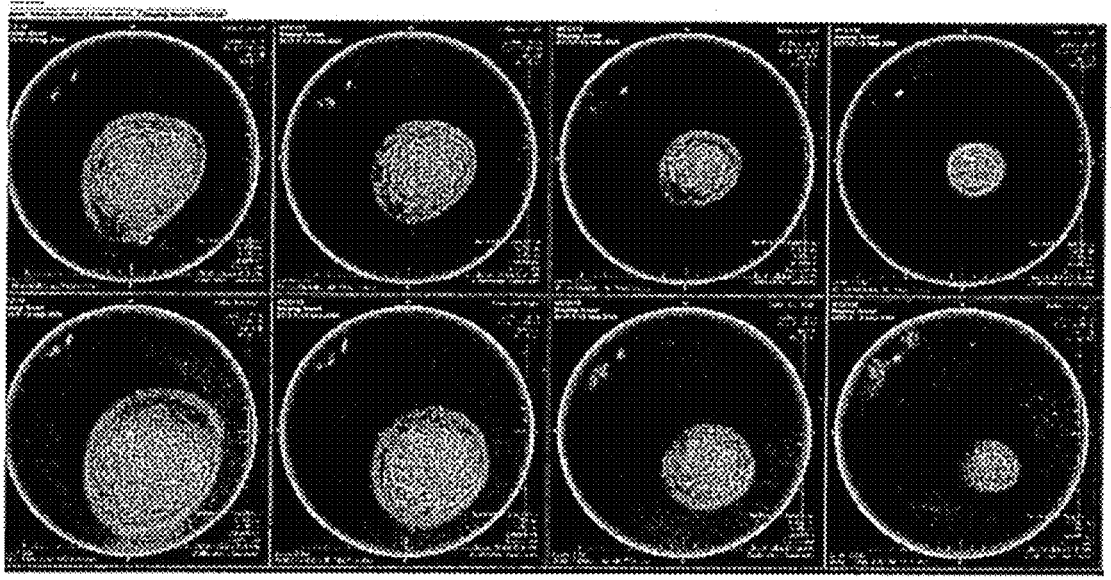

Once the breast has been properly positioned, the ring imaging array 102 and the restrictor ring 174 will be raised to scan the length of the breast as shown in FIGS. 7E through 7G. In FIG. 7E, the circumference of the breast is such that the interior edges of the restrictor ring do not contact the breast. As the assembly of the transducer 102 and ring 172 continues to be raised, as shown in FIG. 7F, the interior edge of the ring 172 will begin to contact the breast and displace the breast away from the interior of the transducer ring 102. As the assembly of the imaging array 102 and restrictor ring 174 rises further, as shown in FIG. 7G, the interior edge of the restrictor ring 174 will significantly displace the breast tissue inwardly, avoiding interference with the imaging function of the array 102.

Example images generated with an ultrasonic tomography system equipped with a BSD of the present invention are shown in FIGS. 8A-8D.

Embodiments of the system, methods, and protocols of the present invention and variations thereof can be embodied and/or implemented at least in part by a machine configured to receive a computer-readable medium storing computer-readable instructions. The instructions are preferably executed by computer-executable components preferably integrated with the system and one or more portions of a processor and/or a controller. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

The FIGURES illustrate the architecture, functionality and operation of possible implementations of systems, methods and computer program products according to preferred embodiments, example configurations, and variations thereof. In this regard, each block in a flowchart or block diagram may represent a module, segment, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A tissue positioning system for contouring a patient tissue volume, the system comprising:
 a tissue interface displaceable along an axis and having a surface configured to engage the tissue volume;
 one or a plurality of plenums disposed on the surface between the radial axis and the outer shell; and
 a low pressure source configured to apply low pressure to the surface of the displaceable interface;
 wherein the low pressure secures the tissue volume to the surface by flowing fluid through the one or the plurality of plenums, and wherein the tissue interface is biased to pull and elongate the tissue volume along the axis when the tissue volume is secured to the surface; and
 a telescoping support attached to a side of the tissue interface opposite to a side engaged by the tissue volume, wherein the telescoping support comprises two or more concentric parts, wherein the two or more concentric parts are configured to slide within one another thereby varying a volume within the two or more concentric parts.

2. A tissue positioning system as in claim 1, further comprising a spring, wherein the spring is extendable along the axis, and wherein the spring is operable to extend the tissue interface along the axis toward the tissue volume.

3. A tissue extension system as in claim 2, wherein the spring comprises a coil spring which is extended when the surface of the tissue interface engages the tissue volume.

4. A tissue positioning system as in claim 3, wherein the low pressure source biases the tissue interface to pull and elongate the tissue volume.

5. A tissue positioning system as in claim 1, wherein the low pressure source is connected to apply the low pressure within the volume within the two or more concentric parts.

6. A tissue positioning system as in claim 5, further comprising a coil spring within the two or more concentric parts of the telescoping support which is extended when the surface of the tissue interface engages the tissue volume and applies a spring force against the tissue volume.

7. A tissue positioning system as in claim 6, wherein the low pressure source is configured to apply sufficient force to pull and elongate the tissue volume against the spring force of the coil spring.

8. A system for scanning a breast tissue volume of a patient, the system comprising:
 a base having a horizontal surface with an opening therein, said base being configured to support the patient in a prone position with a breast disposed through the opening;
 an imaging device disposed below the base and configured to image the breast disposed through the opening;

a tissue interface displaceable along an axis and having a surface configured to engage tissue surrounding a nipple of the breast;

one or a plurality of plenums disposed on the tissue interface surface between the radial axis and the outer shell, oriented radially away from the axis; and a low pressure source configured to apply a low pressure to the surface of the tissue interface; and a telescoping support having an upper end attached to a side of the tissue interface opposite to a side engaged by the breast tissue volume and located within a well;

wherein the telescoping support comprises two or more concentric parts, wherein the two or more concentric parts are configured to slide within one another thereby varying a volume within the two or more concentric parts;

wherein the low pressure secures the breast tissue volume to the surface by flowing a fluid through the one or the plurality of plenums, and wherein the tissue interface is biased to pull and elongate the breast tissue volume along the axis when the breast tissue volume is secured to the surface.

9. A system for scanning a breast tissue volume of a patient as in claim 8, wherein the imaging device comprises an ultrasonic transducer array.

10. A system for scanning a breast tissue volume of a patient as in claim 9, wherein the well is disposed below the opening in the horizontal surface and configured to contain an ultrasonically transmissive medium, wherein the ultrasonic transducer array is located within the well and configured to scan breast tissue within the well.

11. A system for scanning a breast tissue volume of a patient as in claim 8, wherein the low pressure source is connected to apply the low pressure within the two or more concentric parts of the telescoping support to draw and engage the breast tissue volume to the interface.

12. A system for scanning a breast tissue volume of a patient as in claim 11, further comprising a coil spring within the two or more concentric parts of the telescoping support which is extended when the surface of the tissue interface engages the breast tissue volume and thereafter applies tension to the breast tissue volume.

13. A system for scanning a breast tissue volume of a patient as in claim 12, wherein the low pressure source is configured to apply sufficient force to pull and elongate the breast tissue volume against a spring force of the coil spring.

14. A system for scanning a breast tissue volume of a patient as in claim 9, wherein the imaging device comprises an ultrasonic ring imaging array configured to circumscribe and translate over the breast.

15. A system for scanning a breast tissue volume of a patient as in claim 8, wherein the imaging device further comprises a restrictor ring secured over the ultrasonic ring imaging array to circumferentially restrict the breast so that breast tissue volume does not contact the ultrasonic ring imaging array as the ring is translated over the breast.

16. A method for imaging a breast of a patient, the method comprising:

locating the patient in a prone position with the breast disposed downwardly through an opening in a horizontal surface;

engaging a surface of a tissue interface against tissue surrounding a nipple of the breast, wherein the tissue interface is displaceable along an axis;

applying a low pressure to the surface by flowing a fluid through one or a plurality of plenums disposed on the tissue interface surface between the radial axis and the outer shell, oriented radially away from the axis to seal the breast to the tissue interface;

biasing the tissue interface downwardly to elongate and contour the breast; and imaging the breast with a device disposed below the horizontal surface while the breast remains contoured;

wherein the tissue interface is supported by a telescoping support located within a well and having an upper end attached to a lower side of the tissue interface, wherein the telescoping support comprises two or more concentric parts, wherein the two or more concentric parts are configured to slide within one another thereby varying a volume within the two or more concentric parts.

17. A method for imaging a breast of a patient as in claim 16, wherein imaging comprises ultrasonic imaging.

18. A method for imaging a breast of a patient as in claim 16, further comprising immersing the breast in the well, wherein the well contains an ultrasonically transmissive medium disposed below the opening in the horizontal surface, wherein an ultrasonic transducer ring array is located in the well and circumscribes the breast to scan the breast.

19. A method for imaging a breast of a patient as in claim 16, wherein a low pressure source is connected to apply the low pressure within the two or more concentric parts of the telescoping support to draw and engage the breast to the surface of the tissue interface.

20. A method for imaging a breast of a patient as in claim 19, wherein a coil spring within the two or more concentric parts of the telescoping support extends the surface of the tissue interface toward the breast prior to engagement.

21. A method for imaging a breast of a patient as in claim 20, wherein the low pressure source applies sufficient force to pull and elongate the breast against a spring force of the coil spring.

22. A method for imaging a breast of a patient as in claim 16, wherein imaging comprises circumscribing and translating an ultrasonic ring imaging array over the breast.

23. A method for imaging a breast of a patient as in claim 22, wherein the ultrasonic ring imaging array comprises a restrictor ring which displaces the breast so that breast tissue does not contact the ultrasonic ring imaging array as the ring is translated over the breast.

24. A method for imaging a breast of a patient as in claim 22, wherein the one or the plurality of plenums are peripheral plenums configured to distribute a low pressure about the surface's periphery to provide attachment to the periareolar region of the breast.

* * * * *